Figure 1:
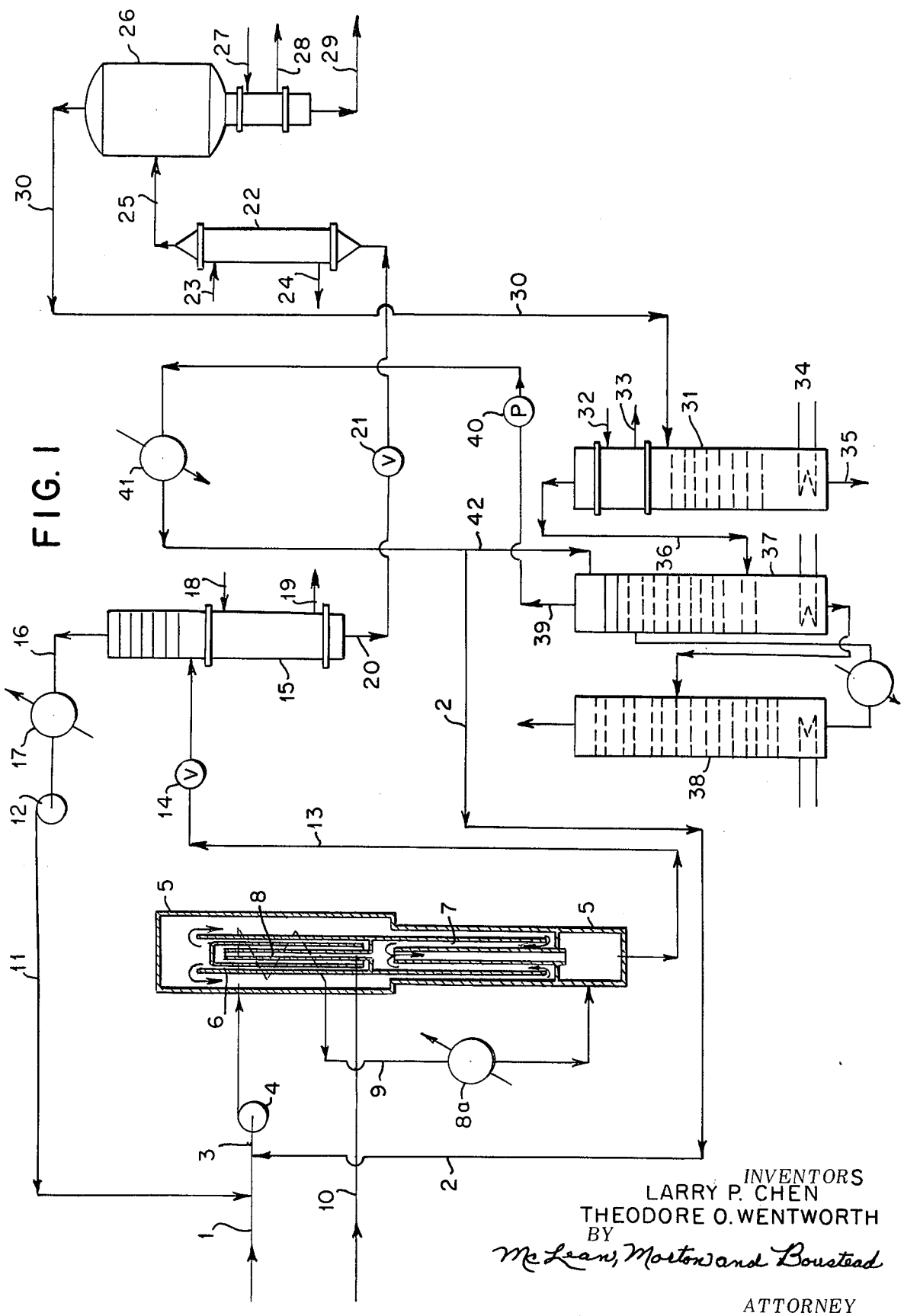

United States Patent [19]

Chen et al.

[11] 3,932,504

[45] Jan. 13, 1976

[54] UREA MANUFACTURE

[75] Inventors: Larry P. Chen; Theodore O. Wentworth, both of Cincinnati, Ohio

[73] Assignee: Vulcan-Cincinnati, Inc., Cincinnati, Ohio

[22] Filed: May 19, 1970

[21] Appl. No.: 38,686

[52] U.S. Cl. ............................................. 260/555 A
[51] Int. Cl.² ....................................... C07C 126/00
[58] Field of Search ................................ 260/555 A

[56] References Cited
UNITED STATES PATENTS

| | | | |
|---|---|---|---|
| 3,046,307 | 7/1962 | Bochinski | 260/555 |
| 3,436,317 | 4/1969 | Otsuka et al | 260/555 |
| 3,470,247 | 9/1969 | Guadalupi | 260/555 |
| 3,527,799 | 9/1970 | Mavrovic | 260/555 |

*Primary Examiner*—James O. Thomas, Jr.
*Assistant Examiner*—A. Siegel
*Attorney, Agent, or Firm*—McLean, Boustead and Sayre

[57] ABSTRACT

Urea is made from ammonia and carbon dioxide by first reacting ammonia and carbon dioxide to form urea, ammonium carbamate and water, and then decomposing the carbamate to ammonia and carbon dioxide which are returned to the reaction zone.

4 Claims, 3 Drawing Figures

U.S. Patent  Jan. 13, 1976  Sheet 1 of 3  3,932,504

INVENTORS
LARRY P. CHEN
THEODORE O. WENTWORTH
BY
McLean, Morton and Boustead
ATTORNEY U.S. Patent   Jan. 13, 1976   Sheet 2 of 3   3,932,504

LARRY P. CHEN
THEODORE O. WENTWORTH
INVENTORS

BY McLean, Morton and Boustead

ATTORNEYS

UREA MANUFACTURE

FIELD OF THE INVENTION

This invention relates to an improved process for making urea from ammonia and carbon dioxide. The process is carried out in a reaction vessel which has a zone in which the ammonia and carbon dioxide are reacted to form urea, ammonium carbamate and water, and which also has a zone in which the carbamate is decomposed to ammonia and carbon dioxide. Liquid ammonia is passed in indirect heat exchange relationship with the mixture in the reaction zone, whereby the mixture is cooled and liquid ammonia is vaporized. Ammonia vapor thus produced is passed into the zone in which carbamate is decomposed into ammonia and carbon dioxide to assist in the decomposition of the carbamate. Ammonia and carbon dioxide vapors produced by the decomposition of the carbamate are returned to the reaction zone. A stoichiometric excess of ammonia (that is, more than two moles of ammonia per mole of carbon dioxide and generally from 2.5 to 10 moles of ammonia per mole of carbon dioxide) is introduced into the reaction vessel, and, optionally, means are provided for the recycle of excess ammonia which passes through the reaction vessel unconverted.

The decomposition of the carbamate to ammonia and carbon dioxide is an endothermic reaction, and heat should therefore be added to the carbamate-containing mixture in order to maintain the mixture undergoing decomposition to ammonia and carbon dioxide at a more appropriate temperature. This is accomplished, in accordance with an embodiment of the invention, by introducing carbon dioxide into the stream leaving the zone in which the ammonia and carbon dioxide are reacted to form urea whereby the excess ammonia present in such stream and the carbon dioxide introduced react to form ammonium carbamate and thereby generate heat, while the stream is in indirect heat-exchange relationship with the zone in which the carbamate is decomposed to ammonia and carbon dioxide.

Also, in accordance with an embodiment of the invention, the urea-containing stream leaving the reaction vessel is flashed at relatively high pressure to produce ammonia vapor, which is conveniently liquefied and returned to the reaction vessel.

DESCRIPTION OF THE PRIOR ART

In U.S. Pat. No. 3,046,307 to Julius H. Bochinski it is proposed to synthesize urea from ammonia and carbon dioxide in a reaction vessel which has a reaction zone in which the ammonia and carbon dioxide react to form urea, ammonium carbamate and water, and which also has a zone in which carbamate is decomposed into ammonia and carbon dioxide which are returned to the reaction zone. Vapors from the reaction zone are cooled and condensed by means of indirect heat exchange and the condensate is returned to the reaction zone. By this means, the reaction zone is cooled and the heat generated therein is dissipated. Gaseous ammonia is introduced into the zone in which the carbamate is decomposed to ammonia and carbon dioxide to aid in the decomposition of the carbamate, and the ammonia and carbon dioxide thus formed are returned to the reaction zone.

Thus, the Bochinski patent describes a process for making urea from ammonia and carbon dioxide in which gaseous ammonia is introduced into a stripping zone for upward flow therein into a reaction zone which is maintained at substantially the same pressure as the stripping zone. Carbon dioxide is introduced into the lower portion of the reaction zone for admixture with ammonia from the stripping zone. The carbon dioxide and ammonia flow upwardly in the reaction zone and countercurrently to an aqueous stream containing ammonium carbamate and urea produced by the reaction of ammonia and carbon dioxide in the reaction zone. This aqueous stream containing ammonium carbamate and urea passes downwardly through the stripping zone countercurrently to the gaseous ammonia which is introduced into the stripping zone for the purpose of decomposing the carbamate to carbon dioxide and ammonia.

The use of a stream of gaseous ammonia for the purpose of decomposing carbamate to ammonia and carbon dioxide is also described in U.S. Pat. No. 3,470,247 to Mario Guadalupi.

SUMMARY OF THE INVENTION

In the present invention, the reaction zone is cooled by passing liquid ammonia into indirect heat exchange relationship with the mixture in the reaction zone. Ammonia vapor is thus formed, and is introduced into the zone in which ammonium carbamate is decomposed into ammonia and carbon dioxide. When the process is operated in this manner, improved operating advantages result.

Thus, the use of steam or other source of heat for vaporizing liquid ammonia for use in decomposing the carbamate to ammonia and carbon dioxide is not necessary. Also, the liquid ammonia can be passed through a thin-walled heat-exchanger positioned in the reaction zone, for the purpose of generating the ammonia vapor introduced into the zone in which the ammonium carbamate is decomposed into ammonia and carbon dioxide.

Figure 2:
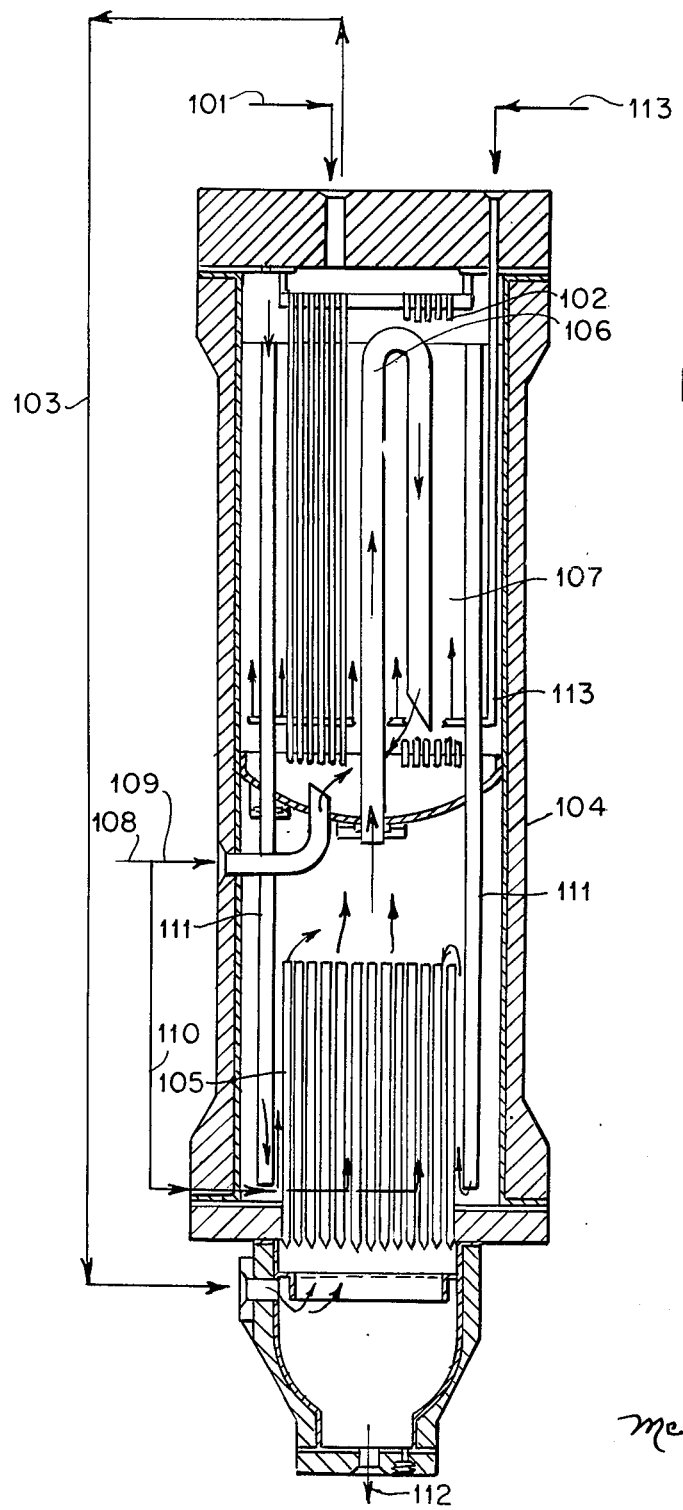
Figure 3:
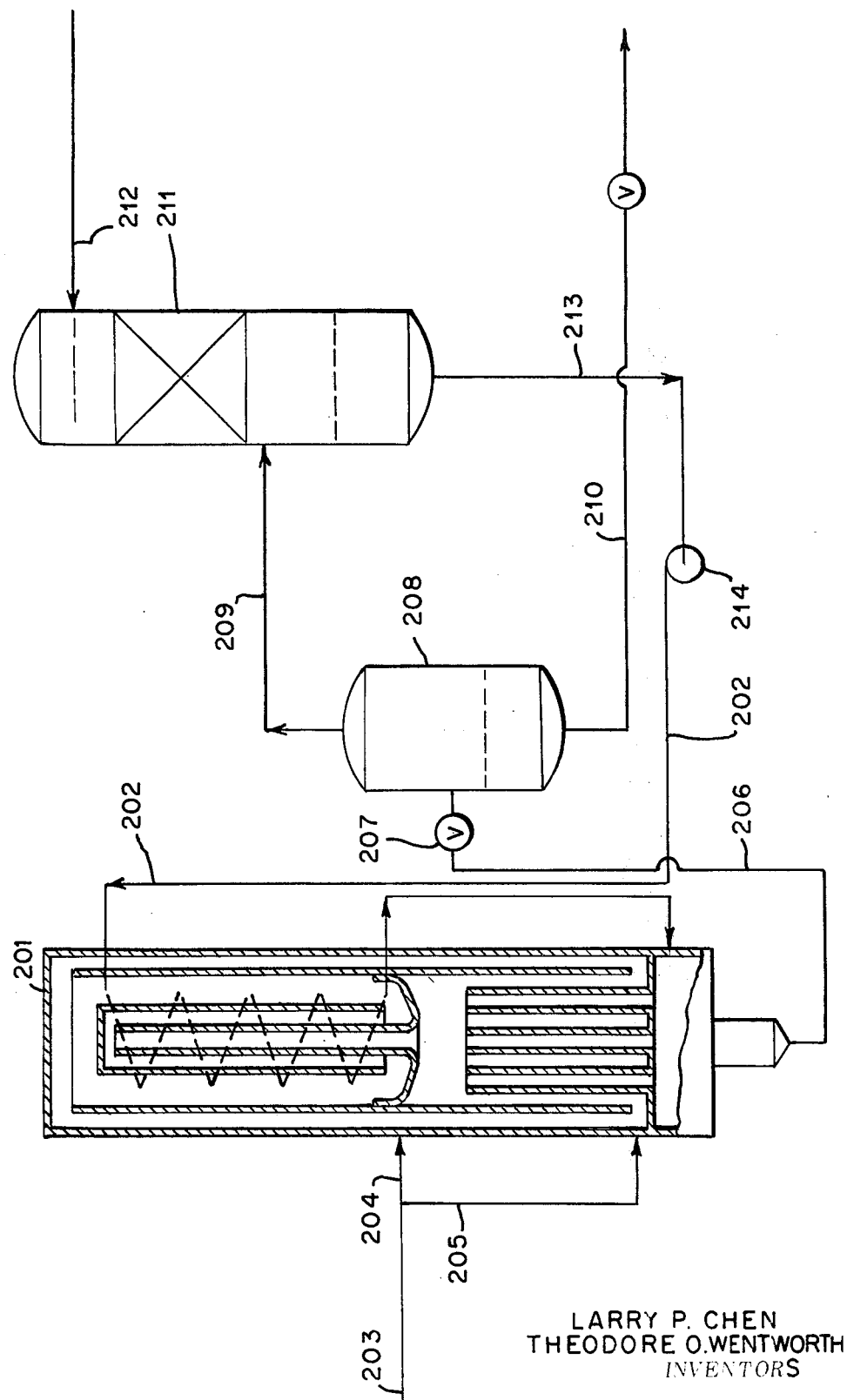

The following description, taken in conjunction with accompanying FIG. 1, FIG. 2, and FIG. 3, describes in detail an operation falling within the broad scope of this invention. FIG. 1 describes a way in which ammonia which passes through the reaction vessel unconverted can be recycled to the reaction vessel with a minimum of power, steam and cooling water consumption. The pound figures mentioned in connection with FIG. 1 are on an hourly basis.

Referring now specifically to FIG. 1, 472 pounds of liquid ammonia flowing through line 1, 93.8 pounds of liquid ammonia flowing through line 2, and 1083.2 pounds of liquid ammonia flowing through line 11 are admixed in line 3 and pressurized by pump 4 to 2750 psig and at a temperature of 100°F. The liquid ammonia is then introduced into vessel 5, which comprises reaction zone 6 and stripping 7. Reaction zone 6 contains an indirect heat-exchanger 8 through which the liquid pumped by pump 4 passes and in which liquid ammonia is vaporized by the heat of the reaction which takes place in reaction zone 6. From heat-exchanger 8 the ammonia vapor, now superheated to a temperature of 320°F, and further heated to a temperature of 360°F., by indirect heat-exchange with steam in heater 8a, is introduced by means of line 9 into the lower portion of stripping zone 7.

Through line 10 there is introduced into the lower portion of reaction zone 6, 642 pounds of carbon dioxide. Reaction zone 6 is at a temperature of about 350°F., and in it there is formed a urea melt containing 830 pounds of urea, 468 pounds of ammonium carbamate, 250 pounds of water and 1117 pounds of dissolved ammonia. This urea melt overflows from the reaction zone 6 and down into the stripping zone 7, where it contacts the ammonia vapor which is introduced into the stripping zone, by means of line 9. As a result of the contacting of the urea melt with the ammonia vapor introduced into the stripping zone there flows upwardly from the stripping zone a vapor mixture of 1792 pounds of ammonia, 234 pounds of carbon dioxide and a trace of water. This vapor mixture then mixes with the carbon dioxide introduced through line 10, and this entire mixture flows upwardly through reaction zone 6 to produce the urea melt previously described.

From the bottom of the stripping zone by means of line 13 there is withdrawn a final urea melt containing 830 pounds of urea, 54.6 pounds of ammonium carbamate, 250 pounds of water and 1154.8 pounds of dissolved ammonia at a temperature of about 340°F, and at a pressure of about 2750 psig. This final urea melt flows through let-down valve 14, which reduces the pressure to 260 psig. The mixture is then introduced into column 15.

Column 15 is operated at 260 psig and in it ammonia vapor is taken overhead by means of line 16. The ammonia vapor passing through line 16 is introduced into cooler 17 and is liquefied therein by indirect heat-exchange with cooling water. Steam is introduced into the lower section of column 15 by means of line 18. Condensate is removed by means of line 19. The purpose of the steam is to vaporize the ammonia by means of indirect heat-exchange.

From the bottom of column 15 through line 20 there is removed a mixture of 830 pounds of urea, 54.6 pounds of ammonium carbamate, 250 pounds of water and 70 pounds of dissolved ammonia. This mixture is at a temperature of 302°F. and at a pressure of 260 psig. The mixture passes through let-down valve 21 and is then introduced into decomposer 22, which is operated at slightly above atmospheric pressure. Decomposer 22 is equipped with a heat-exchanger into which steam is introduced by means of line 23. Condensate is removed by means of line 24. In the decomposer ammonium carbamate is decomposed to form urea and water, so that through line 25 there is introduced into vessel 26, 94.1 pounds of ammonia, 30.8 pounds of carbon dioxide and 158 pounds of water. The lower portion of vessel 26 is provided with a heat-exchanger, into which steam is introduced by means of line 27. Condensate is removed by means of line 28. From the bottom of vessel 26 by means of line 29, there is removed an ammonia-free urea melt containing 830 pounds of urea and 92 pounds of water. This melt can be further processed by conventional means.

The overhead vapor from vessel 26 passes by way of line 30 and is introduced into a stripping and dehumidifying tower 31, the upper section of which is provided with a heat exchanger into which cooling water is introduced by means of line 32 and removed by means of line 33. The tower 31 is also provided with steam coil 34. Water is removed from the bottom of tower 31 by means of line 35, and overhead from tower 31 by means of line 36 there is removed a mixture of 94.1 pounds of ammonia, 30.8 pounds of carbon dioxide and 12.0 pounds of water at a temperature of 155°F.

The mixture flowing through line 36 is introduced into a conventional monoethanolamine absorption-desorption system which includes absorber 37 and desorber 38. From the top of absorber 37 by means of line 39 there is removed 94.1 pounds of ammonia vapor which is pumped by compressor 40 through water-cooled condenser 41 in which the ammonia vapor is liquefied. A portion of this liquid ammonia is returned to absorber 37 as reflux through line 42, and the remainder flows through line 2.

FIG. 2 illustrates a particularly valuable embodiment of the present invention with respect to the operation of the reaction vessel. In the operation shown in FIG. 2, a portion of the carbon dioxide is added to the mixture leaving the urea-forming zone for reaction with ammonia contained therein to produce ammonium carbamate and generate heat which is transferred to the zone in which carbamate is decomposed to ammonia and carbon dioxide.

In FIG. 2, liquid ammonia from an outside source is introduced by means of line 101 into heat-exchanger tubes 102 wherein the liquid ammonia is vaporized and passes by means of line 103 into the bottom of the generally cylindrical reaction vessel indicated by the numeral 104. The ammonia vapor then passes upwardly through heat-exchanger tubes 105 and then through line 106 and into the reaction zone 107.

Carbon dioxide from an outside source passes by means of line 108, 109 and 110 into the reaction vessel 104, the amount of carbon dioxide passing through line 109 in general being from 70 to 90% of that passing through line 108. The carbon dioxide passing through line 109 enters the reaction zone 107, wherein a mixture containing urea, ammonium carbamate and water is formed. The mixture also contains excess ammonia. The reaction mixture passes upwardly through the reaction zone 107 and overflows downwardly through lines 111 into admixture with the carbon dioxide introduced through line 110. The carbon dioxide and ammonia react to form ammonia carbamate and generate heat.

The mixture passes upwardly outside heat-exchanger tubes 105 and then flows downwardly through the heat-exchanger tubes 105 countercurrent the gaseous ammonia introduced through line 103, resulting in the decomposition of ammonium carbamate to ammonia and carbon dioxide. The mixture leaving the bottom of vessel 104 can be processed by known procedures for the recovery of urea. If desired, some of the ammonia used in the operation can be introduced by means of line 113 directly into the reaction mixture.

Table I which follows sets forth operating data obtained using the procedure described in FIG. 2. In obtaining the data of Table I, no ammonia was introduced through line 113, and 80% of the carbon dioxide passed through line 108 passed through line 109. In Table I, the carbon dioxide in stream 112 is in the form of ammonium carbamate, that is, it is in chemical combination with a portion of the ammonia present in that stream.

TABLE I

| Run No. | I | | II | | | III | | | IV | | | |
|---|---|---|---|---|---|---|---|---|---|---|---|---|
| Stream No | 108 | 103 | 112 | 108 | 103 | 112 | 108 | 103 | 112 | 108 | 103 | 112 |
| | | | | | Percent, By Weight | | | | | | | |
| $CO_2$ | 100 | 0 | 1.87 | 100 | 0 | 1.18 | 100 | 0 | 1.62 | 100 | 0 | 0.66 |
| $NH_3$ | 0 | 100 | 48.33 | 0 | 100 | 53.17 | 0 | 100 | 51.39 | 0 | 100 | 48.55 |
| $H_2O$ | 0 | 0 | 12.42 | 0 | 0 | 10.88 | 0 | 0 | 10.48 | 0 | 0 | 12.28 |
| Urea | 0 | 0 | 37.38 | 0 | 0 | 34.77 | 0 | 0 | 36.51 | 0 | 0 | 38.51 |
| Total | 100 | 100 | 100.00 | 100 | 100 | 100.00 | 100 | 100 | 100.00 | 100 | 100 | 100.00 |
| Press., PSIG | 3050 | 3050 | 3000 | 2850 | 2850 | 3800 | 2750 | 2750 | 2700 | 3050 | 3050 | 3000 |
| Temp., °F | 240 | 362 | 340 | 236 | 354 | 338 | 232 | 360 | 341 | 241 | 363 | 342 |
| $NH_3/CO_2$ Feed Mole Ratio | | | 6.14 | | | 7.05 | | | 6.50 | | | 6.30 |
| Overall Urea/(urea + $CO_2$) Mole Fraction | | | 0.936 | | | 0.9545 | | | 0.939 | | | 0.979 |

FIG. 3 illustrates a particularly valuable embodiment of the present invention wherein the urea-containing mixture leaving the bottom of the reaction vessel (operating pressure generally between 2000 and 8000 psig), passes through a pressure letdown valve whereby the pressure of the mixture is reduced to a pressure within the range from 1000 psig to just below the critical pressure of ammonia (1623.2 psig). The mixture then passes to a flash vessel or drum, overhead from which there is removed a stream of essentially pure gaseous ammonia. As bottoms from the flash vessel there is removed a liquid stream containing ammonia, water, urea and a small amount of carbon dioxide in the form of ammonium carbamate. This liquid stream can be further processed, for example, as described in FIG. 1 or by means well known in the art.

Operation of the flash vessel or drum at high pressure, but below the critical pressure of ammonia, results in definite operating advantages. Thus, the ammonia vapor requires aa relatively small amount of cooling water or other cooling means to condense it for return to the urea synthesis zone. Preferably, the ammonia vapor from the flash vessel is liquefied by direct contact with the fresh liquid ammonia introduced into the urea synthesis zone. By operating in this manner, the vessel used to liquefy the ammonia vapor can be of very simple and inexpensive construction. Moreover, the liquefied ammonia is at a high pressure, and is therefore easily pumped back into the urea synthesis zone. Also, the liquefied ammonia is at a relatively high temperature. Thus when the ammonia is returned to the synthesis zone a heater such as 8a in FIG. I can be eliminated.

Referring now to FIG. 3 in greater detail, the numeral 201 represents a reaction vessel similar to that described in FIG. I and having an upper reaction zone and a lower stripping zone. The vessel is operated at 2750 psig. Liquid ammonia at a temperature of 220°F is introduced into vessel 201 by means of line 202 and carbon dioxide is introduced through lines 203, 204 and 205, the amount of carbon dioxide flowing through line 204 being four times that flowing through line 205.

From the bottom of vessel 201 through line 206 there is removed a liquid mixture having a temperature of 350°F and containing 830 pounds of urea, 54.6 pounds of ammonium carbamate, 250 pounds of water, and 1154.8 pounds of ammonia, the amounts being in pounds per hour. The mixture flowing through line 206 passes through letdown valve 207, which reduces the pressure to 1400 psig, and then into flash vessel 208. Due to the flashing the temperature is reduced to 310°F. 510 pounds per hour of essentially pure ammonia vapor passes through line 209, and through line 210, there flows 830 pounds of urea, 54.6 pounds of ammonium carbamate, 250 pounds of water and 644.8 pounds of ammonia, the amounts being in pounds per hour.

In vessel 211 the ammonia vapor passing through line 209 is directly contacted with liquid ammonia having a temperature of 105°F, introduced through line 212 at the rate of 1139 pounds per hour. As a result, there flows through line 213 ammonia liquid (temperature of 220°F) at the rate of 1649 pounds per hour. This liquid ammonia is pumped by pump 214 into vessel 201 by means of line 202.

Table II sets forth operating data obtained using the procedure described in FIG. 3. Table II gives the results of four runs (a, b, c and d) wherein the stream passing through line 206 was flashed by means of letdown valve 207 to pressures of 1600, 1400, 1200 and 1000 psig, respectively. Vessel 201 was operated under essentially constant conditions for the four runs and four-fifths of the carbon dioxide flowing through line 203 also flowed through line 204. Here again, the carbon dioxide in streams 206 and 210 is combined with a portion of the ammonia in the form of ammonium carbamate.

TABLE II

| Stream No. | 203 | 202 | 206 |
|---|---|---|---|
| | | Percent, By Weight | |
| $CO_2$ | 100 | 0 | 1.79 |
| $NH_3$ | 0 | 100 | 47.83 |
| $H_2O$ | 0 | 0 | 12.29 |
| Urea | 0 | 0 | 38.09 |
| Total | 100 | 100 | 100.00 |
| Press., psig. | 2900 | 2900 | 2850 |
| Temp., °F | 245 | 360 | 350 |
| $NH_3/CO_2$ Feed Mole Ratio | | 6.01 | |
| Overall Urea/(urea+$CO_2$) mole Fraction | | 0.9397 | |

| Stream No. | 210a | 210b | 210c | 210d |
|---|---|---|---|---|
| | | Percent, By Weight | | |
| $CO_2$ | 2.04 | 2.81 | 2.88 | 1.78 |
| $NH_3$ | 38.66 | 34.06 | 32.30 | 31.23 |
| $H_2O$ | 13.02 | 14.38 | 14.07 | 15.53 |
| Urea | 45.76 | 48.75 | 50.75 | 51.46 |
| Total | 100.00 | 100.00 | 100.00 | 100.00 |
| Press., psig. | 1600 | 1400 | 1200 | 1000 |
| Temp., °F | 315 | 310 | 300 | 290 |

| Stream No. | 209a | 209b | 209c | 209d |
|---|---|---|---|---|
| | | Percent, By Weight | | |
| $CO_2$ | 144 ppm | 167 ppm | 180 ppm | 243 ppm |

TABLE II-continued

| Stream No. | 203 | 202 | | 206 |
|---|---|---|---|---|
| | | Percent, By Weight | | |
| NH₃ | 100 | 100 | 100 | 100 |
| H₂O | Trace | Trace | Trace | Trace |
| Urea | Not Detected | Not Detected | Not Detected | Not Detected |
| Press., psig. | 1600 | 1400 | 1200 | 1000 |
| Temp., °F | 315 | 310 | 300 | 290 |

What is claimed is:

1. In a process for making urea from ammonia and carbon dioxide wherein gaseous ammonia is introduced into a stripping zone for upward flow therein into a reaction zone maintained at substantially the same pressure as the stripping zone, wherein carbon dioxide is introduced into the lower portion of the reaction zone for admixture with ammonia from the stripping zone, wherein the carbon dioxide and ammonia are flowed upwardly in the reaction zone and countercurrently to an aqueous stream containing ammonium carbamate and urea, wherein the carbon dioxide and ammonia are reacted in the reaction zone to form ammonium carbamate, urea and water, wherein the amount of ammonia introduced into the reaction zone is in excess of that stoichiometrically required to react with the carbon dioxide introduced into the reaction zone in producing urea, wherein said aqueous stream containing ammonium carbamate and urea is passed downwardly through the stripping zone countercurrently to the gaseous ammonia introduced thereinto to decompose the carbamate to carbon dioxide and ammonia for passage with the carbon dioxide fed into the reaction zone, and wherein said reaction zone is cooled by means of indirect heat exchange, the improvement which comprises passing liquid ammonia into indirect heat exchange with the reactants in said reaction zone whereby liquid ammonia is made gaseous and introducing gaseous ammonia thus formed into said stripping zone.

2. The process of claim 1 wherein carbon dioxide is introduced into said aqueous stream containing ammonium carbamate and urea to react with ammonia present in said aqueous stream to produce ammonium carbamate and thereby generate heat, while said aqueous stream is in indirect heat-exchange relationship with said stripping zone whereby the decomposition of the carbamate present in the stripping zone to carbon dioxide and ammonia is promoted.

3. The process of claim 2 wherein the amount of carbon dioxide introduced into said aqueous stream containing ammonium carbamate is from 10 to 30 percent of the total amount of carbon dioxide utilized in the process.

4. The process of claim 1 wherein the urea-containing mixture leaving the stripping zone is flashed to a pressure between 1000 psig and a pressure slightly below the critical pressure of ammonia to provide ammonia vapor and a liquid phase containing urea, liquefying the ammonia vapor by direct contact with fresh ammonia liquid being fed to the reaction zone, and returning the ammonia liquid thus formed directly to the reaction zone.

* * * * *